United States Patent
Deshays

(10) Patent No.: US 8,636,950 B2
(45) Date of Patent: *Jan. 28, 2014

(54) MEDICAL INSTRUMENT DISINFECTING CHAMBER VIA RADIATION

(75) Inventor: Clement Deshays, Ruoms (FR)

(73) Assignee: Germitec, Clichy (FR)

( * ) Notice: Subject to any disclaimer, the term of this patent is extended or adjusted under 35 U.S.C. 154(b) by 640 days.

This patent is subject to a terminal disclaimer.

(21) Appl. No.: 12/067,700

(22) PCT Filed: Dec. 5, 2005

(86) PCT No.: PCT/FR2005/003031
§ 371 (c)(1),
(2), (4) Date: Mar. 21, 2008

(87) PCT Pub. No.: WO2007/034040
PCT Pub. Date: Mar. 29, 2007

(65) Prior Publication Data
US 2008/0213139 A1 Sep. 4, 2008

(30) Foreign Application Priority Data
Sep. 21, 2005 (FR) .................... 05 09649

(51) Int. Cl.
*A61L 2/00* (2006.01)
*A61L 9/00* (2006.01)
*B01J 19/08* (2006.01)
*B01J 19/12* (2006.01)

(52) U.S. Cl.
USPC .................... 422/24; 422/186.3; 422/300

(58) Field of Classification Search
USPC .................... 422/24, 186.3
See application file for complete search history.

(56) References Cited

U.S. PATENT DOCUMENTS

| | | | |
|---|---|---|---|
| 4,772,795 A | 9/1988 | Sakurai et al. | |
| 4,948,566 A | 8/1990 | Gabele et al. | |
| 5,185,532 A | 2/1993 | Zabsky et al. | |
| 5,310,524 A | 5/1994 | Campbell et al. | |
| 5,610,811 A | 3/1997 | Honda | |
| 5,641,464 A | 6/1997 | Briggs, III et al. | |
| 5,690,113 A | 11/1997 | Sliwa, Jr. et al. | |
| 5,761,069 A | 6/1998 | Weber et al. | |
| 5,912,818 A | 6/1999 | McGrady et al. | |
| 6,039,928 A | 3/2000 | Roberts | |
| 6,171,559 B1 * | 1/2001 | Sanders et al. ............... 422/300 |

(Continued)

FOREIGN PATENT DOCUMENTS

| | | |
|---|---|---|
| DE | 32 09 701 A1 | 9/1983 |
| DE | 3917876 A1 | 12/1990 |

(Continued)

OTHER PUBLICATIONS

Machine Translation of DE3209701 from esp@cenet online database (accessed Sep. 20, 2010).*

(Continued)

*Primary Examiner* — Walter D Griffin
*Assistant Examiner* — Christopher Vandeusen
(74) *Attorney, Agent, or Firm* — Morrison & Foerster LLP

(57) ABSTRACT

A medical instrument disinfecting chamber in which one or several instruments are suspended and a disinfecting radiation is generated. A radiation-transparent element maintains the instrument in an extended state substantially vertically oriented, under the suspension.

4 Claims, 1 Drawing Sheet

(56) References Cited

U.S. PATENT DOCUMENTS

| | | | |
|---|---|---|---|
| 6,231,819 B1 * | 5/2001 | Morello | 422/186.3 |
| 6,260,560 B1 | 7/2001 | Walta | |
| 6,371,326 B1 | 4/2002 | Gabele et al. | |
| 6,475,433 B2 | 11/2002 | McGeorge et al. | |
| 6,485,979 B1 | 11/2002 | Kippenhan et al. | |
| 6,641,781 B2 | 11/2003 | Walta | |
| 6,712,756 B1 | 3/2004 | Kura et al. | |
| 7,694,814 B1 | 4/2010 | Cristobal et al. | |
| 7,965,185 B2 | 6/2011 | Cambre et al. | |
| 7,982,199 B2 | 7/2011 | Deshays | |
| 8,313,017 B2 | 11/2012 | Deshays | |
| 8,334,521 B2 | 12/2012 | Deshays | |
| 8,356,745 B2 | 1/2013 | Deshays | |
| 2001/0024623 A1 | 9/2001 | Grimm et al. | |
| 2002/0161460 A1 | 10/2002 | Noguchi | |
| 2002/0162972 A1 * | 11/2002 | Pleet | 250/492.1 |
| 2003/0016122 A1 | 1/2003 | Petrick | |
| 2003/0039579 A1 | 2/2003 | Lambert et al. | |
| 2003/0091471 A1 | 5/2003 | Lacabanne | |
| 2003/0187586 A1 | 10/2003 | Katzenmaier et al. | |
| 2004/0009091 A1 | 1/2004 | Deal et al. | |
| 2004/0140347 A1 | 7/2004 | Mihaylov et al. | |
| 2004/0197248 A1 * | 10/2004 | Hasegawa et al. | 422/297 |
| 2004/0209223 A1 | 10/2004 | Beier et al. | |
| 2005/0196314 A1 | 9/2005 | Peterson et al. | |
| 2007/0027459 A1 | 2/2007 | Horvath et al. | |
| 2008/0213139 A1 | 9/2008 | Deshays | |
| 2008/0219899 A1 | 9/2008 | Deshays | |
| 2009/0065034 A1 | 3/2009 | Suzuki et al. | |
| 2009/0169436 A1 | 7/2009 | Deshays | |
| 2010/0138234 A1 | 6/2010 | Deshays | |
| 2010/0140134 A1 | 6/2010 | Deshays | |
| 2010/0140342 A1 | 6/2010 | Deshays | |
| 2010/0145721 A1 | 6/2010 | Deshays | |

FOREIGN PATENT DOCUMENTS

| | | |
|---|---|---|
| DE | 44 20 707 A1 | 12/1994 |
| DE | 195 14 284 A1 | 10/1996 |
| DE | 19703823 C1 | 5/1998 |
| DE | 19917206 A1 | 10/2000 |
| DE | 10225232 A1 | 12/2002 |
| DE | 10225857 A1 | 1/2004 |
| EP | 0 471 530 A1 | 2/1992 |
| EP | 0630820 A1 | 12/1994 |
| EP | 0 709 056 A1 | 5/1996 |
| EP | 0 709 056 B1 | 5/1996 |
| EP | 0 839 537 A | 5/1998 |
| EP | 1 155 654 A1 | 11/2001 |
| EP | 1 402 904 A1 | 3/2004 |
| EP | 1532989 A1 | 5/2005 |
| FR | 2753905 A1 | 4/1998 |
| FR | 2 890 864 A1 | 3/2007 |
| FR | 2890566 A1 | 3/2007 |
| FR | 2890865 A1 | 3/2007 |
| WO | 8400009 A | 1/1984 |
| WO | 9908137 A1 | 2/1999 |
| WO | WO-99/66444 A2 | 12/1999 |
| WO | WO-01/80908 A1 | 11/2001 |
| WO | WO-2004/111917 A1 | 12/2004 |
| WO | WO-2005/048041 A2 | 5/2005 |
| WO | WO-2005/048041 A3 | 5/2005 |
| WO | WO-2006/115177 A1 | 11/2006 |
| WO | WO-2007/016101 A1 | 2/2007 |
| WO | WO-2007/034083 A1 | 3/2007 |

OTHER PUBLICATIONS

International Search Report of PCT/FR2005/003031, date of mailing Mar. 21, 2006.
International Search Report mailed on Feb. 23, 2009, for PCT Application No. PCT/FR2008/000465, filed on Apr. 3, 2008, 3 pages.
International Search Report mailed on Feb. 23, 2009, for PCT Application No. PCT/FR2008/000464, filed on Apr. 3, 2008, 3 pages.
International Search Report mailed on Jul. 18, 2006, for PCT Application No. PCT/FR2005/003034, filed on Dec. 5, 2005, 3 pages.
International Search Report mailed on Jan. 22, 2009, for PCT Application No. PCT/FR2008/000540, 3 pages.
International Search Report mailed on Jan. 22, 2009, for PCT Application No. PCT/FR2008/000541, 3 pages.
International Search Report mailed on Sep. 11, 2007, for PCT Application No. PCT/FR2007/000594, 3 pages.
International Search Report mailed on Jul. 6, 2006, for PCT Application No. PCT/FR2005/003032, 3 pages.

* cited by examiner

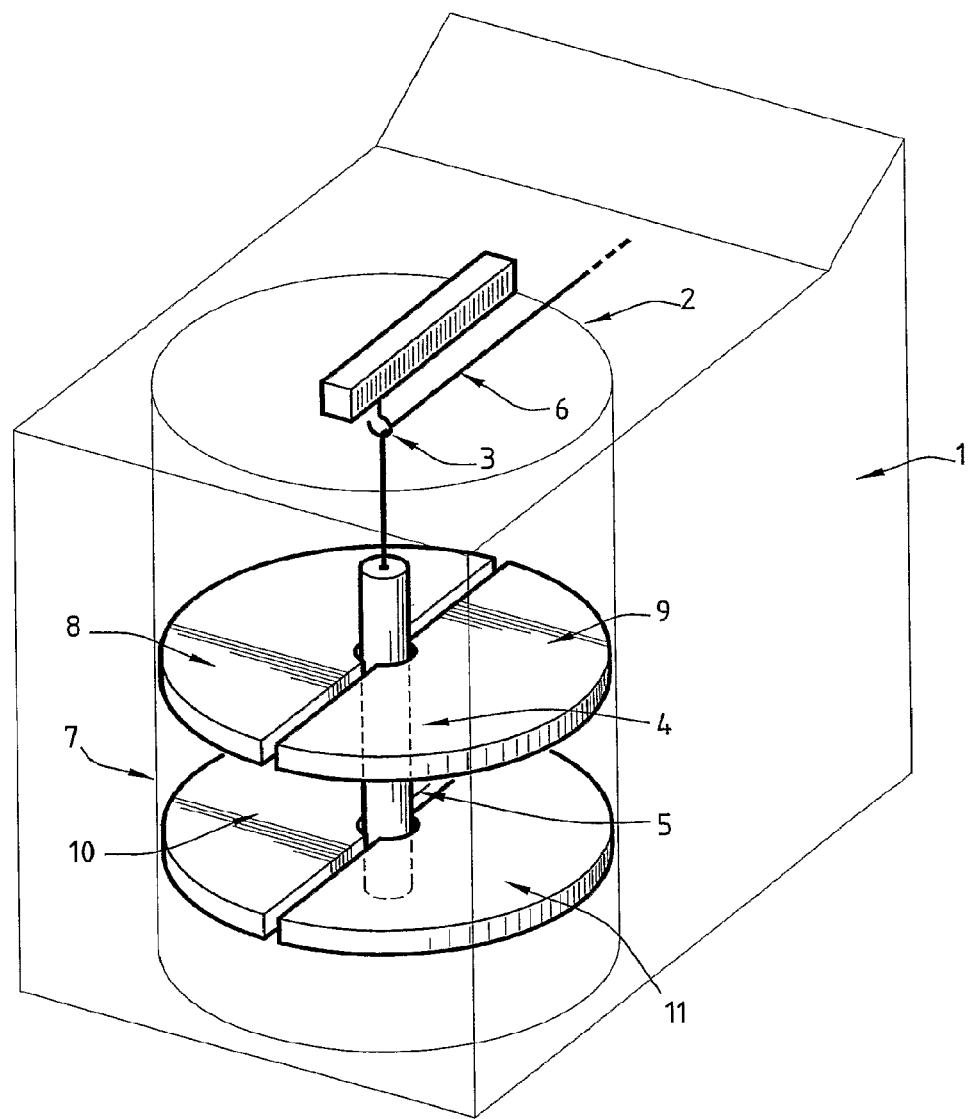

MEDICAL INSTRUMENT DISINFECTING CHAMBER VIA RADIATION

The present invention concerns a medical instrument disinfecting chamber.

More particularly, the invention relates to such a chamber which includes means for suspending at least one instrument in this chamber.

A decontaminating chamber for medical instruments is already known in the art, for example, from document EP-A-0 839 537, which is delimited by a bottom, at least one lateral wall, and an upper lid, each instrument having an active portion and a connecting portion in the form of a cable.

This chamber also includes a boom extending within and at the upper portion of the chamber, parallel to the bottom and overhanging the bottom, this boom including a plurality of suspension members, each of which is intended to cooperate with a portion of the cable neighboring the active portion of the instrument.

Thus, such suspension means make it possible to hold an instrument in the chamber in a position substantially vertical without contact, so as to ensure that it is perfectly disinfected.

That is, it is known that suspending instruments without contact during their disinfection ensures the disinfection quality. However, this type of structure has a number of drawbacks, in particular with respect to the homogeneity of disinfection, especially when the chamber is equipped with means for generating UV radiation, for example, C type UV radiation, making it possible to ensure the disinfection of the instruments.

Further, it can also happen that, for one reason or another, the instrument, which is, for example, in the form of a sensor or other, is entwined with itself or deformed so that all or part of the instrument can then be in a position and/or a state unfavorable to its disinfection.

The objective of the invention is to remedy these problems.

To this effect, an object of the invention is a medical instrument disinfecting chamber, of the type including means for suspending at least one instrument in the chamber and means for generating a disinfecting radiation in the chamber, characterized in that it includes means, transparent to radiation, for holding the instrument in an elongated state and in a substantially vertical orientation, under the suspension means.

According to particular embodiments, the chamber according to the invention can include one or more of the following characteristics:
- the holding means are adapted to hold the instrument substantially at the center of the chamber;
- the holding means comprise means for guiding the instrument in the chamber;
- the guiding means comprise one or several members in the form of combs for guiding the instrument, which are distributed over the height of the chamber;
- the guiding means comprise one or several tubes for receiving the instrument;
- the holding means comprise a weight adapted to be coupled to the free end of the instrument; and
- the holding means are made in silicium oxide.

The invention will be better understood by reading the following description which is given by way of example only, in reference to the annexed drawing which shows a schematic synoptic view illustrating the structure and operation of a disinfecting chamber according to the invention.

That is, this FIGURE illustrates a medical instrument disinfecting chamber.

This chamber is designated by the general reference numeral 1 on this FIGURE and it includes means for generating a disinfecting radiation, such as, for example, an UV radiation, for example, a C type UV radiation.

An example of embodiment of such a chamber is described in the document EP-A-0839537, to which reference can be made for manufacturing details of this chamber.

The chamber described in this document actually includes a boom which is designated by the general reference numeral 2 on this FIGURE and which extends within and at the upper portion of the chamber, parallel to the bottom and overhanging the bottom of this chamber.

That is, the boom is part of the constitution of means for suspending at least one instrument to be disinfected in the chamber.

Advantageously, these suspension means can be, for example, adjustable in height in the chamber, by any mechanism known in the art, such as, for example, a screw-nut device that an operator can maneuver using a knob.

Of course, other embodiments can be envisioned.

In the example of embodiment illustrated on the FIGURE, the suspension means also comprise a member in the form of a hook designated by the general reference numeral 3 to which the instrument designated by the general reference numeral 4 can be suspended.

Actually, this instrument is a medical instrument which can be in the form of a sensor or other, which includes, for example, an active portion designated by the general reference numeral 5 and a connecting cable designated by the general reference 6 making it possible to hang this instrument.

When the means for generating the disinfecting radiation are activated, they make it possible to ensure that the instrument is disinfected by the action of the radiation.

The Applicant has already proposed in other patent applications various improvements to this type of chamber, in particular, by providing specific shapes for the chamber, specific coatings of this chamber, specific movements of the instrument, and also means making it possible to ensure the traceability of the disinfecting operation.

To further improve the quality of disinfection in the chamber according to the invention, means, transparent to radiation, are provided for holding the instrument in an elongated state and a substantially vertical orientation, under the suspension means.

This makes it possible, for example, to avoid any deformation or twisting of the instrument, which could result in a disposition and/or a state of this instrument unfavorable to its disinfection.

Various embodiments of these means for holding the instrument can be envisioned.

Actually, these holding means are adapted to hold the instrument preferably substantially at the center of the chamber, as illustrated.

Then, these holding means can include, for example, means for guiding the instrument such as those illustrated on this FIGURE and designated by the general reference numeral 7.

That is, in the example of embodiment illustrated on this FIGURE, these holding means comprise one or several members in the form of guiding combs distributed over the height of the chamber, to hold the instrument in an optimal position for disinfection.

In the illustrated example, two series of two complementary combs designated by the reference numerals 8, 9, 10 and 11, respectively, are used at two different heights in the chamber to hold the instrument in the optimal position.

Of course, it is understood that other embodiments of these means can be envisioned. Thus, by way of example, one or several tubes for receiving one or several instruments can also be envisioned, these tubes extending, for example, in the area of the center of the chamber in a vertical position.

However, according to still another embodiment, these holding means can also be formed by a weight adapted to be coupled and/or suspended at the corresponding free end of the instrument so as to hold this instrument in position.

Of course, as indicated above, these holding means are made of material transparent to radiation such as, for example, C type UV radiation.

In this case, the holding means are made, by way of example, in silicium oxide.

Of course, it is understood that other embodiments can be envisioned.

Holding the instrument in position in this way makes it possible to ensure that it is in the most favorable position possible for its disinfection in the chamber.

The invention claimed is:

1. Medical instrument disinfecting chamber, comprising:
a bottom, at least one lateral wall, and an upper portion,
a suspension member for suspending at least one instrument in the chamber, said suspension member extending at the upper portion of the disinfecting chamber,
a disinfecting radiation source in the chamber, and
a plurality of complementary holders for holding the instrument comprising two or more sets of complementary holders that are distributed over the height of the chamber to hold the instrument in an elongated state and in a substantially vertical orientation, under the suspension member,
wherein said plurality of complementary holders are transparent to radiation, and
wherein said plurality of holders are located under said suspension member and comprise a portion located in a central area of the disinfecting chamber under the suspension member, in a path of radiation emitted by the radiation source toward the center of the disinfecting chamber.

2. Medical instrument disinfecting chamber according to claim 1, wherein the portion of the holders located in the central area of the disinfecting chamber comprises a central guide area.

3. Medical instrument disinfecting chamber according to claim 1, wherein the holders comprise guiding combs that are distributed over the height of the chamber.

4. Medical instrument disinfecting chamber according to claim 1, wherein the holders are made of silicium oxide.

* * * * *